US012653633B2

(12) United States Patent
Simi et al.

(10) Patent No.: US 12,653,633 B2
(45) Date of Patent: Jun. 16, 2026

(54) STERILE ADAPTER FOR A ROBOTIC SURGERY SYSTEM, ASSEMBLY, SYSTEM AND METHOD

(71) Applicant: MEDICAL MICROINSTRUMENTS, INC., Pisa (IT)

(72) Inventors: Massimiliano Simi, Pisa (IT); Giorgio Lazzari, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 769 days.

(21) Appl. No.: 17/929,008

(22) PCT Filed: Feb. 10, 2021

(86) PCT No.: PCT/IB2021/051073
§ 371 (c)(1),
(2) Date: Aug. 10, 2022

(87) PCT Pub. No.: WO2021/161184
PCT Pub. Date: Aug. 19, 2021

(65) Prior Publication Data
US 2023/0082871 A1 Mar. 16, 2023

(30) Foreign Application Priority Data
Feb. 10, 2020 (IT) ........................ 102020000002536

(51) Int. Cl.
*A61B 34/37* (2016.01)
*A61B 90/00* (2016.01)

(52) U.S. Cl.
CPC .............. *A61B 34/37* (2016.02); *A61B 90/08* (2016.02)

(58) Field of Classification Search
CPC ................... A61B 34/30; A61B 34/37; A61B 2017/00477
See application file for complete search history.

(56) References Cited

U.S. PATENT DOCUMENTS

| | | | |
|---|---|---|---|
| 5,682,264 A | 10/1997 | Cleveland et al. | |
| 6,024,454 A | 2/2000 | Horan et al. | |
| (Continued) | | | |

FOREIGN PATENT DOCUMENTS

| | | | |
|---|---|---|---|
| EP | 0591936 A1 | 4/1994 | |
| WO | 2009061915 A1 | 5/2009 | |
| (Continued) | | | |

OTHER PUBLICATIONS

Bernard, Stylo-bille M10 Bic—Bernard, Sep. 20, 2016, URL: https://www.youtube.com/watch?v=0n494qih6ZI, retrieved Oct. 2, 2020.
(Continued)

*Primary Examiner* — Todd J Scherbel
(74) *Attorney, Agent, or Firm* — Armstrong Teasdale LLP

(57) ABSTRACT

A sterile adapter for a robotic surgery system includes a frame, a proximal coupling device suitable to form a connection with a non-sterile robotic manipulator system, a distal cavity suitable to form a connection with a surgical instrument suitable to perform robotic surgery to a patient anatomy, and a membrane having a proximal non-sterile side and a distal sterile side opposite to the proximal non-sterile side. The membrane is between the proximal coupling device and the distal cavity, and membrane is stretchable to transmit a plurality of pushing actions from the proximal non-sterile side to the distal sterile side. The frame is rigid to transmit a roll action.

8 Claims, 8 Drawing Sheets

(56) References Cited

U.S. PATENT DOCUMENTS

| | | | |
|---|---|---|---|
| 9,204,933 B2 | 12/2015 | Reis et al. | |
| 9,456,876 B2 | 10/2016 | Hagn | |
| 10,321,964 B2 | 6/2019 | Grover et al. | |
| 2007/0064309 A1 | 3/2007 | Luloh et al. | |
| 2009/0248039 A1 | 10/2009 | Cooper et al. | |
| 2009/0248040 A1 | 10/2009 | Cooper et al. | |
| 2010/0082041 A1 | 4/2010 | Prisco | |
| 2012/0289973 A1 | 11/2012 | Prisco et al. | |
| 2015/0173840 A1 | 6/2015 | Lohmeier | |
| 2016/0151115 A1 | 6/2016 | Karguth et al. | |
| 2018/0325616 A1 | 11/2018 | Kapadia et al. | |
| 2019/0053866 A1 | 2/2019 | Seow et al. | |
| 2019/0231448 A1 | 8/2019 | Mcbrien et al. | |
| 2021/0137618 A1* | 5/2021 | Simi | A61B 34/37 |

FOREIGN PATENT DOCUMENTS

| | | | |
|---|---|---|---|
| WO | 2011143024 A1 | 11/2011 | |
| WO | 2016081286 A1 | 5/2016 | |
| WO | 2016137611 A1 | 9/2016 | |
| WO | 2016178028 A1 | 11/2016 | |
| WO | 2017015599 A1 | 1/2017 | |
| WO | 2017064303 A1 | 4/2017 | |
| WO | 2017064306 A1 | 4/2017 | |
| WO | 2017205308 A1 | 11/2017 | |
| WO | 2017205333 A1 | 11/2017 | |
| WO | 2018189721 A1 | 10/2018 | |
| WO | 2018189722 A1 | 10/2018 | |
| WO | 2018189729 A1 | 10/2018 | |
| WO | 2019006206 A1 | 1/2019 | |
| WO | 2019150086 A1 | 8/2019 | |

OTHER PUBLICATIONS

International Search Report and Written Opinion for International Patent Application No. PCT/IB2021/051073, mailed May 4, 2021, 11 pp.

* cited by examiner

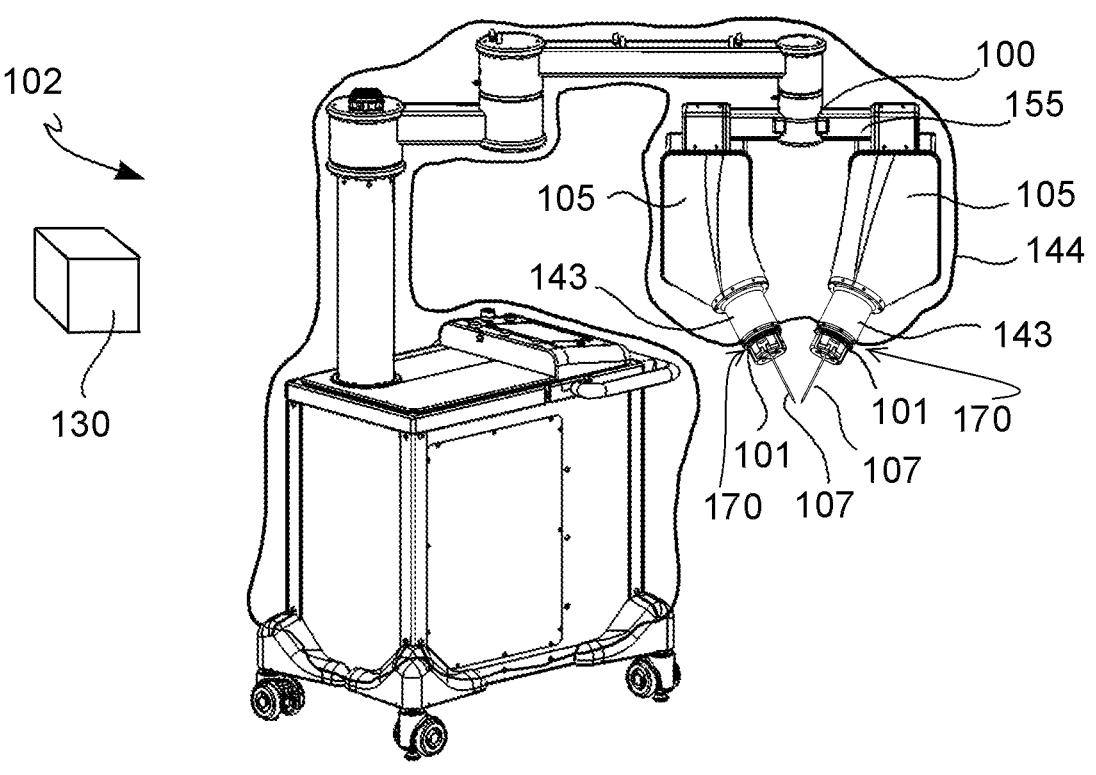
FIG. 1
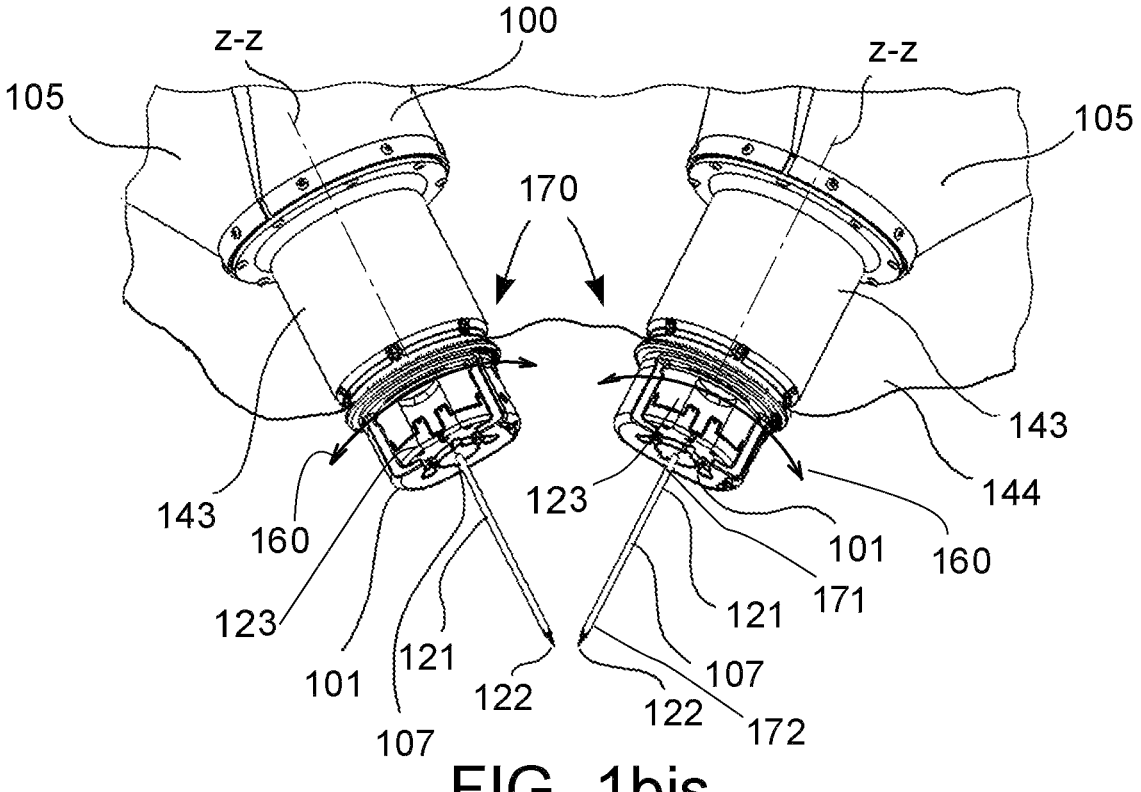
FIG. 1bis

STERILE ADAPTER FOR A ROBOTIC SURGERY SYSTEM, ASSEMBLY, SYSTEM AND METHOD

CROSS-REFERENCE TO RELATED APPLICATIONS

This application is a National Stage Application of International Patent Application No. PCT/IB2021/051073, having an International Filing Date of Feb. 10, 2021, which claims priority to Italian Application No. 102020000002536, filed Feb. 10, 2020, each of which is hereby incorporated by reference in its entirety.

FIELD OF THE INVENTION

It is an object of the present invention a sterile adapter for a robotic surgery system.

In particular, the present invention relates to a sterile adapter suitable to connect to a surgical instrument for robotic surgery.

The present invention also relates to a robotic surgery system.

The present invention also relates to a slave assembly for a robotic surgery system.

The present invention also relates to a method.

BACKGROUND

Robotic surgery apparatuses are generally known in the art and typically comprise at least one tele-operated robotic arm having a robotic motorized positioning system for moving a surgical end effector distally attached thereto, in order to perform surgical procedures to a patient. The need of miniaturization is strongly felt in the technical field of robotic surgery, particularly in microsurgery and laparoscopic surgery to reduce the invasiveness on the patient. Documents WO-2017-064303, WO-2017-064306, WO-2018-189721 and WO-2018-189722 in the name of the same Applicant disclose various solutions able to miniaturize the surgical end-effector by means of reduction of the size of the wrist of the surgical instrument attached at the distal end of the instrument shaft.

The patient typically lies on an operatory bed located in an operatory room, wherein sterilization is ensured in order to avoid bacterial contamination due to the non-sterile parts of the robotic tele-operated system. Usually, a surgical drape wraps the robot in order to protect the sterile environment from contamination. The need of wrapping the robot arise from the fact that such robot must be used for several interventions. The surgical drape may be provided with inserts, like rigid plastic plates, in order to form a connection interface with an active part of the robot.

For example, document WO-2011-143024 shows a solution of a sterile drape having annular external rim rotatably connected to another portion of the sterile drape having reciprocal annular opening, thereby forming a two-pieced sterile drape, wherein the sterile adapter has an inner frame describing a cross figure delimiting four cloves or slices, each clove receiving a pocket made of drape material, and wherein each pocket has rigid plates attached distally thereto, each plate having a capstan for transmitting through said plates a rotatable actuation actions from the robot to the surgical instrument. Those pockets comprise each an extra amount of drape material allowing to extend the pockets.

This document also shows four additional sterile adapters attached distally to the four pockets and engaged with said rigid plates of the pockets.

Usually, a sterilized surgical end-effector, for example a clamp and/or a blade designed to operate on the patient, is attached at the active part of the robot through the connection interface of the sterile drape, as shown for example in document WO-2016-137611. Therefore, the sterile drape is required to have a connection interface able to transmit action from the robot to the end-effector. In the above-mentioned example, the connection interface is provided with windows to permit a rack-and-pinion direct contact through each of said windows. Furthermore, sterile drapes can comprise also fixation strings that allow tying the sterile drape to close-fit an elongated portion of the robot, such as a robotic elongated arm, thereby reducing the volume of the sterile drape when in use. Examples are also known providing magnetic attachment between the robot and the drape.

The connection interface or adapter of the barrier, designed to transmit the actuation, may also be in form of foldable, frusto-conical cuffs designed to individually receive a motor piston, and those cuffs may be glued or otherwise secured to the active parts of the robot, as shown for example in document WO-2019-006206. However, this known solution does not solve the problem and forces to glue the sterile barrier to the distal face of the non-sterile actuators. Tearing or breaking of the barrier material may result from the relative motion of the components required for transmission across the barrier, for example when such a transmission involves hoists or capstans, for example designed to wind multiple times in order to transmit motion. Pockets individually receiving a piston require very high deformation of each of the pockets, the drape material of the pockets results prone to tear if the drape material is not deformable enough or if it is deformable enough implies crumble of the drape material of each pocket during retraction of the piston individually received therein. Moreover, this known solution shows a sterile adapter having a rectangular box-shaped external body having a "C" shape delimiting an inner through hole defined by the "C"-shaped adapter body itself to receive the surgical instrument, which has to be inserted from the proximal side passing through such inner trough hole along a direction coincident with the longitudinal extension of the shaft of the surgical instrument, and that in turn requires to further reduce the usable surface area of each pocket.

Document US-2019-0231448 discloses a solution where three parallel male linear sliders engaged across a detachable rubber element with respective three parallel female sliders in order to transmit a linear displacement action parallel to the free surface of the detachable rubber element across the detachable rubber element. The detachable rubber element is detachably mounted on a surface of a rigid frame, the rigid frame having a circular external rim, and surface which the rubber element is detachably mounted to is orthogonal to the circular external rim and spaced from the circular rim in the distal direction.

Sterile adapters or interfaces are also known for example from documents: WO-2009-061915, WO-2016-081286, WO-2016-178028, WO-2017-015599, WO-2017-205308, WO-2017-205333, WO-2019-150086, EP-0591936, EP-3025667, U.S. Pat. Nos. 5,682,264, 6,024,454, 9,204,933, 9,456,876, U.S. Ser. No. 10/321,964, US-2007-064309, US-2009-248039, US-2009-248040, US-2010-082041, US-2012-289973, US-2015-173840, US-2016-151115, US-2018-325616 and US-2019-053866.

Document WO-2018-189729 in the name of the same Applicant shows a sterile barrier solution involving stiffening elements attached thereto, with the purpose of transmitting linear actuation across the barrier itself. The surface of the stiffening elements may be rounded to guarantee a single point contact with the non-sterile actuators. Despite advantageous for several reasons, such a solution results difficult to manufacture and to assemble because of the requested alignment of actuators, stiffening elements and actuated elements.

Therefore, the need is felt to provide a solution for the transmission of an actuating action across a sterile barrier, without for this reason tearing the barrier.

It is felt the need of providing a sterile adapter able to detachably couple a surgical instrument for robotic surgery to a manipulator, so that to allow removal and exchange of the surgical instrument in a sterile operatory field.

Solution

It is a scope of the present invention to overcome the drawbacks mentioned with reference to the known art.

These and other scopes are achieved by a sterile adapter, a slave robot assembly, a robotic surgery system, and a method as described and claimed herein.

According to an aspect of the invention, a sterile adapter for a robotic surgery system is suitable to transmit a plurality of linear actuation actions and a roll action from a non-sterile robotic manipulator system to a sterile surgical instrument having a backend portion and a shaft extending from said backend portion.

The sterile adapter may be devoid of relatively movable parts to transmit said plurality of linear actuation actions and said roll action.

According to an aspect of the invention, the sterile adapter comprises a frame for transmitting the roll action from the non-sterile robotic manipulator system to the sterile surgical instrument, the frame comprising a proximal coupling device, for coupling with the non-sterile robotic manipulator system, and a distal coupling device, for coupling with the sterile surgical instrument, wherein said frame delimits a through opening between said proximal coupling device and said distal coupling device. The frame may be the outer frame of the sterile adapter. The opening may be circular.

According to an aspect of the invention, the sterile adapter comprises a membrane fixed to said frame sealing said through opening forming a distal cavity between said stretchable membrane and said distal coupling device of the frame.

According to an aspect of the invention, the membrane is designed for transmitting through the thickness thereof the plurality of localized linear actuation actions from the non-sterile robotic manipulator to the sterile surgical instrument.

According to an aspect of the invention, said membrane is elastically stretchable with the purpose to result elastically biased towards a substantially flat configuration thereof.

According to an aspect of the invention, said distal cavity is suitable for receiving at least a portion of the backend of the sterile surgical instrument, said distal coupling device comprises at least one abutment surface facing said stretchable membrane and thereby at least partially delimiting said distal cavity, said at least one abutment surface is suitable for a portion of the surgical instrument to abut thereon. For example, when in use, the backend of the surgical instrument abuts against said at least one abutment surface. Said at least one abutment surface may be located beneath the stretchable membrane, such as under the encumber of the membrane.

The plurality of localized linear actuation actions may be able to exert a pushing action to load the surgical instrument against said at least one abutment surface.

Said distal cavity may include lateral guiding surfaces apt to mate with at least one lateral countersurface of said sterile surgical instrument, and preferably said lateral guiding surfaces of the distal cavity of the sterile adapter is substantially flat. Said lateral guiding surfaces are preferably non-parallel to the membrane, and more preferably orthogonal to the membrane. Said distal cavity may include a lateral opening designed for inserting said sterile surgical instrument into the sterile adapter. The insertion direction of the surgical instrument is therefore non-parallel to the shaft of the surgical instrument, and preferably is orthogonal to the shaft of the surgical instrument. Said distal coupling device may be designed to snap-fit engage with a portion of a surgical instrument, for example a portion of the backend and/or a portion of the shaft.

Said distal cavity may include a second lateral opening suitable to access the distal cavity with the purpose of pushing said sterile surgical instrument out from said distal cavity of the sterile adapter. Thereby also the detachment direction of the surgical instrument is non-parallel to the shaft of the surgical instrument, and preferably is orthogonal to the shaft of the surgical instrument.

Said membrane may be a single flat piece of material. Said membrane may be shaped as a disc. Said membrane may be integrally mounted to said frame so that not to rotate with respect of the frame. Said proximal coupling device and said distal coupling device of said frame may be made as a single piece. Said proximal coupling device and said distal coupling device of said frame may be devoid of any relative degree of freedom. Said frame may rigidly determine the reciprocal positioning and orientation of said proximal coupling device and said distal coupling device and preferably also of the lateral opening of the distal coupling device.

Said distal coupling device of the frame may define a distal seat having a distal through opening that opens distally outside of the distal cavity. Said distal through opening may be substantially aligned with the through opening that is sealed by the stretchable membrane, and may be coaxial with the through opening that is sealed by the stretchable membrane.

A flagging device may be provided flagging when the sterile adapter is coupled to the robotic manipulator system. The flagging device may comprise a flagging pin comprising a distal flagging end, protruding cantilevered from the frame body of the sterile adapter when the sterile adapter is coupled to the robotic manipulator system.

According to an aspect of the invention, a slave robot assembly for a robotic surgery system comprises a non-sterile robotic manipulator system, a sterile surgical instrument having a backend portion and a shaft extending from said backend portion, and a sterile adapter, suitable to transmit a plurality of linear actuation actions and a roll action from said non-sterile robotic manipulator system to said sterile surgical instrument, wherein said sterile adapter comprises a frame transmitting the roll action from the non-sterile robotic manipulator system to the sterile surgical instrument, and wherein said frame comprises a proximal coupling device, coupled with the non-sterile robotic manipulator system, and a distal coupling device, coupled with the sterile surgical instrument, and wherein said frame delimits a through opening between said proximal coupling device and said distal coupling device, and wherein said sterile adapter comprises a membrane fixed to said frame, transmitting through the thickness of the membrane the plurality of localized linear actuation actions from the non-sterile robotic manipulator to the sterile surgical instrument, and wherein said membrane is elastically stretchable with the purpose to result elastically biased towards a substantially flat configuration thereof, and wherein said stretchable membrane seals said through opening forming a distal cavity between said stretchable membrane and said distal coupling device; and wherein said distal cavity receives at least a portion of the backend of the sterile surgical instrument; and wherein said distal coupling device comprises at least one abutment surface facing said stretchable membrane and thereby at least partially delimiting said distal cavity; and wherein the surgical instrument abuts against said at least one abutment surface.

The surgical instrument may abut against additional abutment surfaces formed by the frame of the sterile adapter and delimiting said cavity and facing said membrane.

The geometric centre of the membrane may be aligned with the shaft of the sterile surgical instrument.

The plurality of localized linear actuation actions may be directed orthogonally to a proximal surface and to a distal surface of the membrane. A plurality of pistons may be provided in said robotic motorized manipulator exerting said plurality of localized linear actuation actions. The pistons preferably extend orthogonally to the membrane.

The sterile adapter when in use may rotate together with the sterile surgical instrument, in other words the sterile adapter and the surgical instrument are integral in rotation when the roll action is transmitted to said frame of the sterile adapter.

The non-sterile robotic manipulator system may comprise a plurality of linear actuators, such as said plurality of pistons, and the membrane may be elastically preloaded against the distal end of at least one of said plurality of linear actuators when said at least one linear actuator of said plurality of linear actuators advances distally. For example, when said at least one linear actuator of said plurality of linear actuators retracts, the membrane may be detached from the distal end of said at least one linear actuator of said plurality of linear actuators. The backend of the surgical instrument may comprise a plurality of linear transmission elements individually aligned with the pistons of said plurality of pistons.

The plurality of localized linear actuation actions may be aligned with the shaft of the surgical instrument. Thereby the plurality of linear actuators, such as said plurality of pistons, are aligned to the shaft, as well as the plurality of transmission elements, such as rods, of the backend are aligned to the shaft.

The sterile adapter may be detachably coupled with said non-sterile robotic manipulator system. The surgical instrument may be detachably coupled with said sterile adapter.

The slave robot assembly may comprise at least a rotary joint transmitting said roll action to the surgical instrument by means of said frame of the sterile adapter. The slave assembly may comprise at least one roll motor, the roll motor may be operatively connected to said rotary joint.

A robotic surgery system may comprise said slave robot assembly and a master console controlling said slave robot assembly.

According to an aspect of the invention, a method for transmission of a roll action and of a plurality localized linear displacement actions across a sterile barrier comprises the step of providing a sterile adapter comprising a frame and a stretchable membrane fixed to said frame, the stretchable membrane being part of the sterile barrier, and the step of transmitting said roll action by means of the frame of the sterile adapter, and the step of transmitting said plurality of localized linear displacement actions by means of the membrane, through the thickness thereof. Each of the steps of transmitting said roll action and of transmitting said plurality of localized linear displacement actions may comprise transmitting to a surgical instrument.

The stretchable membrane may be a single membrane receiving said plurality of linear displacement action localized at various locations on the proximal surface of the single membrane.

Said plurality of localized linear displacement actions may be directed orthogonally to a proximal surface of the stretchable membrane.

FIGURES

Further characteristics and advantages of the sterile adapter, the assembly, the system and the method will appear from the description reported below of preferred embodiments, which are given as examples and are not meant to be limiting, which makes reference to the attached figures, in which:

FIG. 1 shows an axonometric view of a robotic surgery system, according to an embodiment;

FIG. 1b is is a view of a detail of FIG. 1, showing two sterile adapters;

DETAILED DESCRIPTION OF SOME EMBODIMENTS

Figures 2, 3:
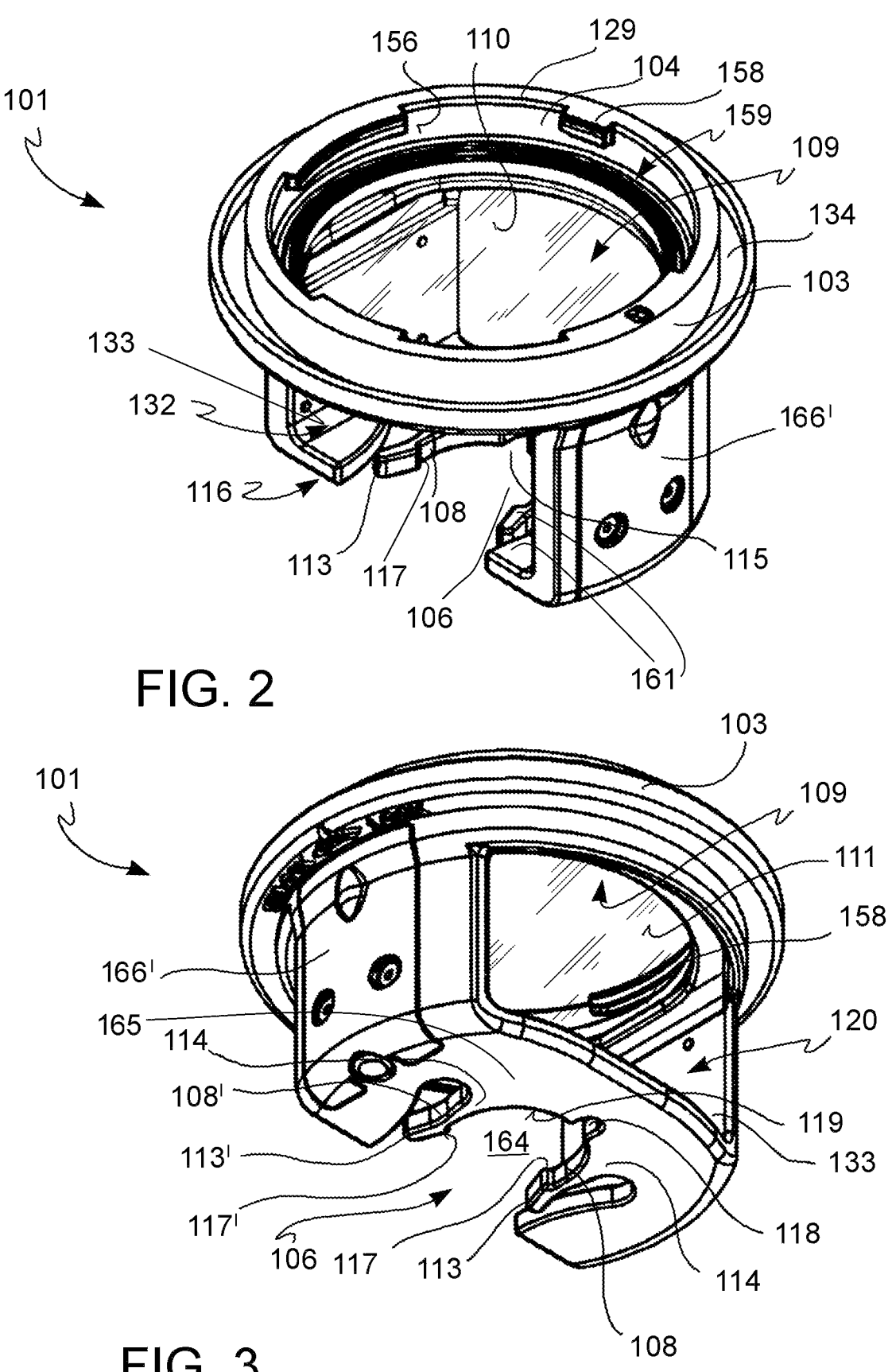
FIGS. 2 and 3 show axonometric views of a sterile adapter, according to an embodiment.
Figure 4:
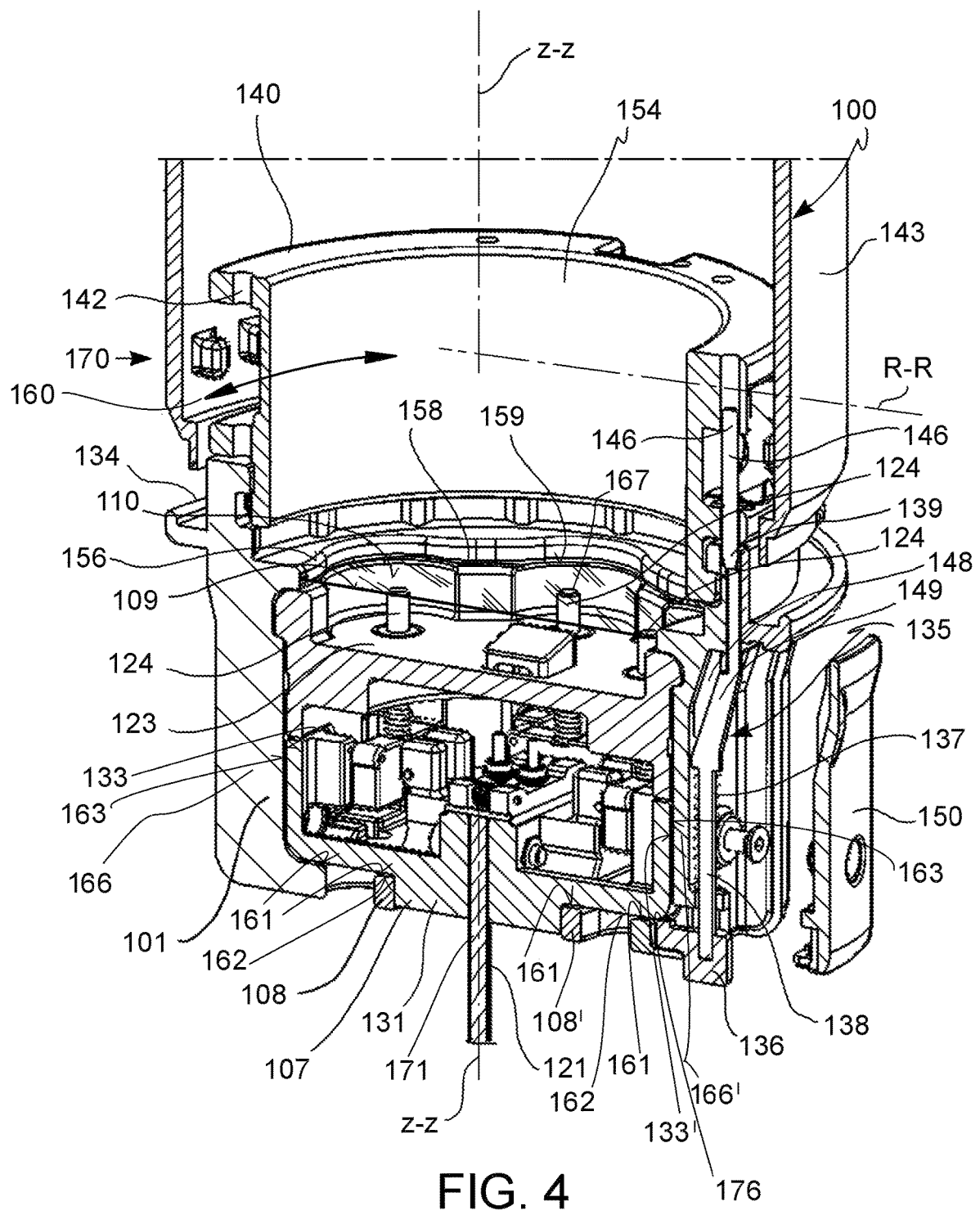
FIG. 4 shows a cross section of a sterile adapter coupled to a robotic manipulator system and a surgical instrument, according to an embodiment, wherein some parts of the manipulator system are transparent for sought of clarity.
Figure 5:
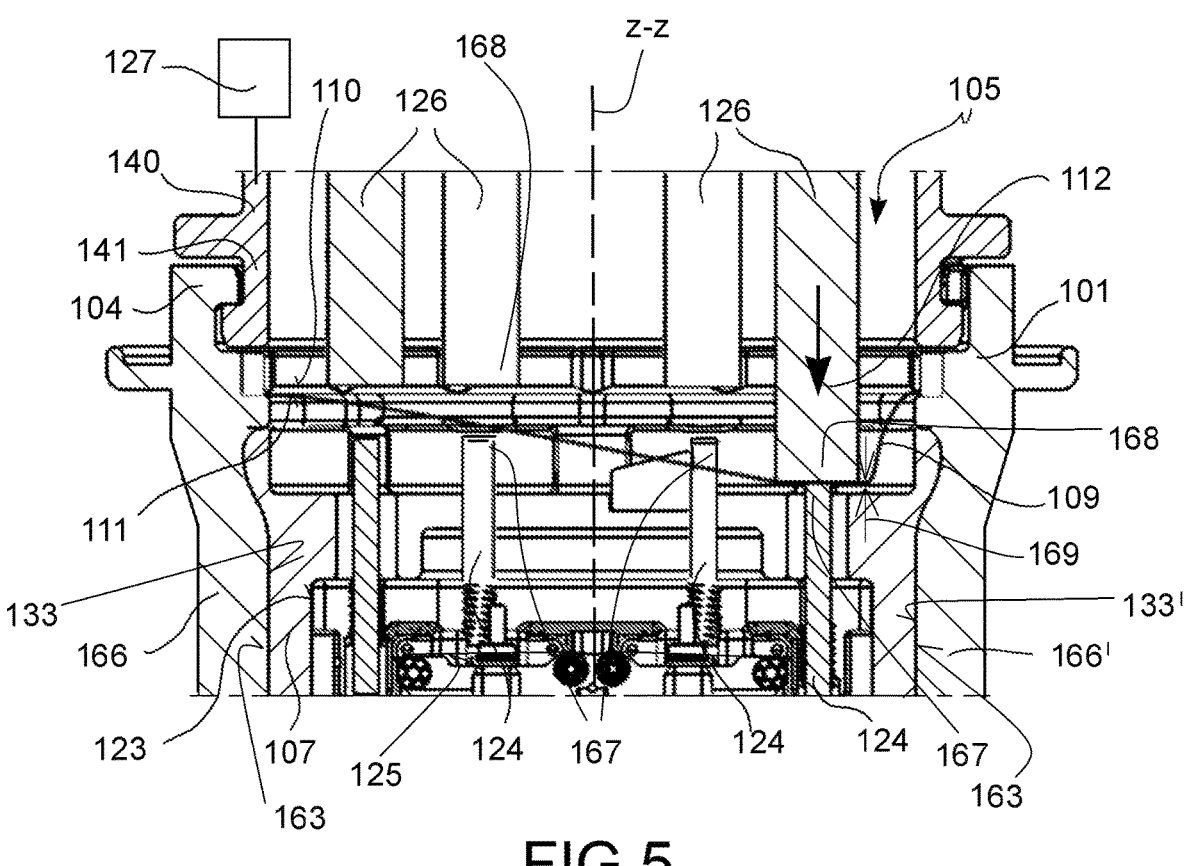
FIG. 5 shows diagrammatically a cross section of a slave assembly having a sterile adapter, a connector, a robotic manipulator system and a surgical instrument, according to an embodiment.
Figure 6:
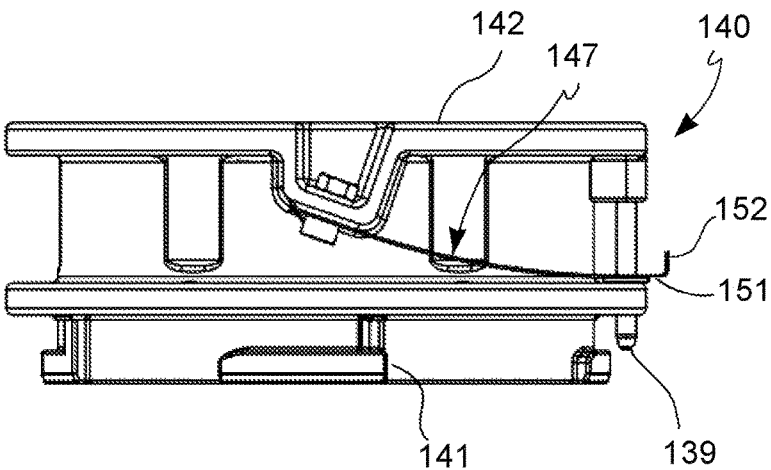
FIG. 6 shows as side view a portion of a connector of a slave assembly, according to an embodiment.
Figure 7:
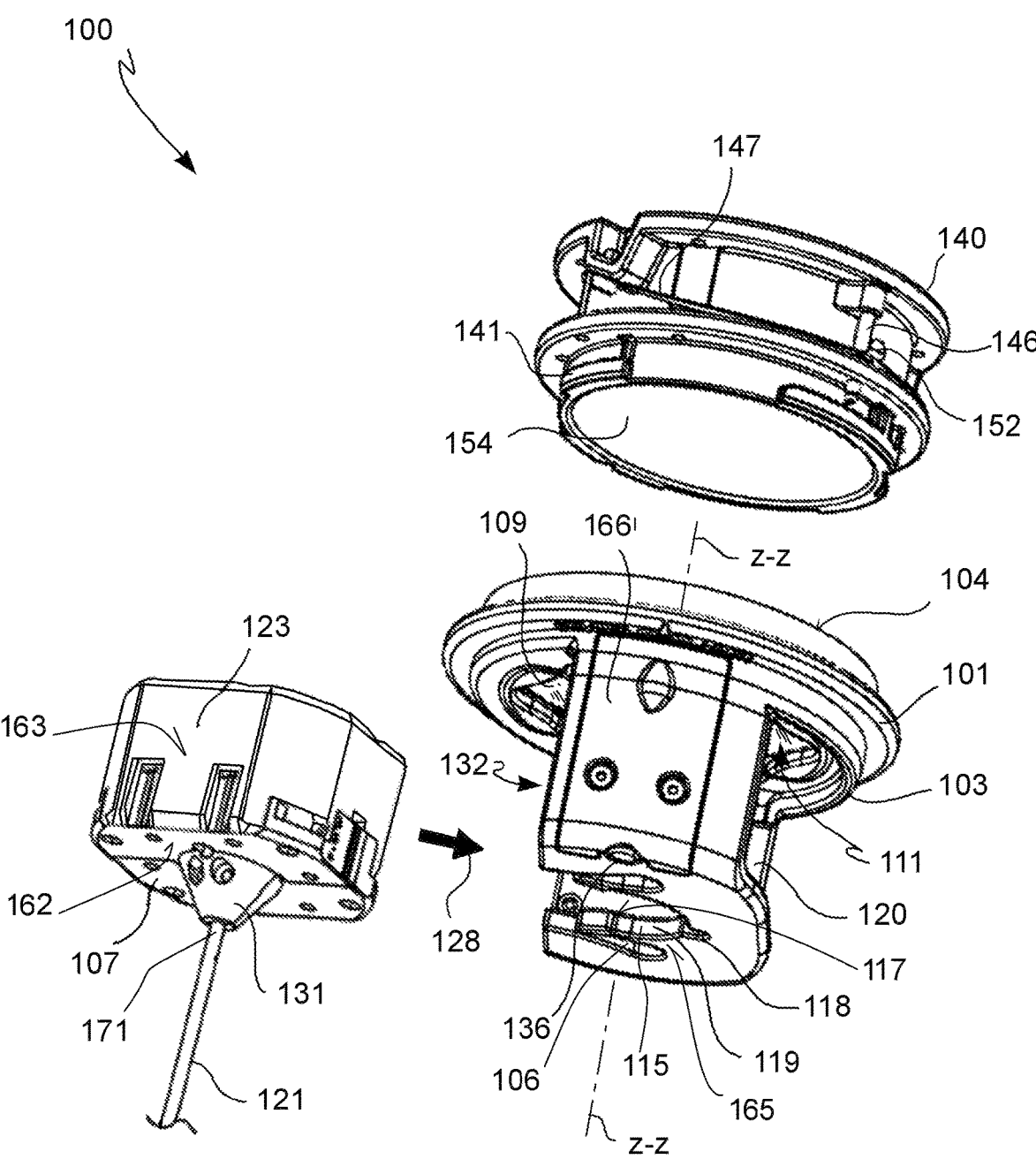
FIG. 7 shows an axonometric view of a slave assembly as separated parts, according to an embodiment.
Figure 8:
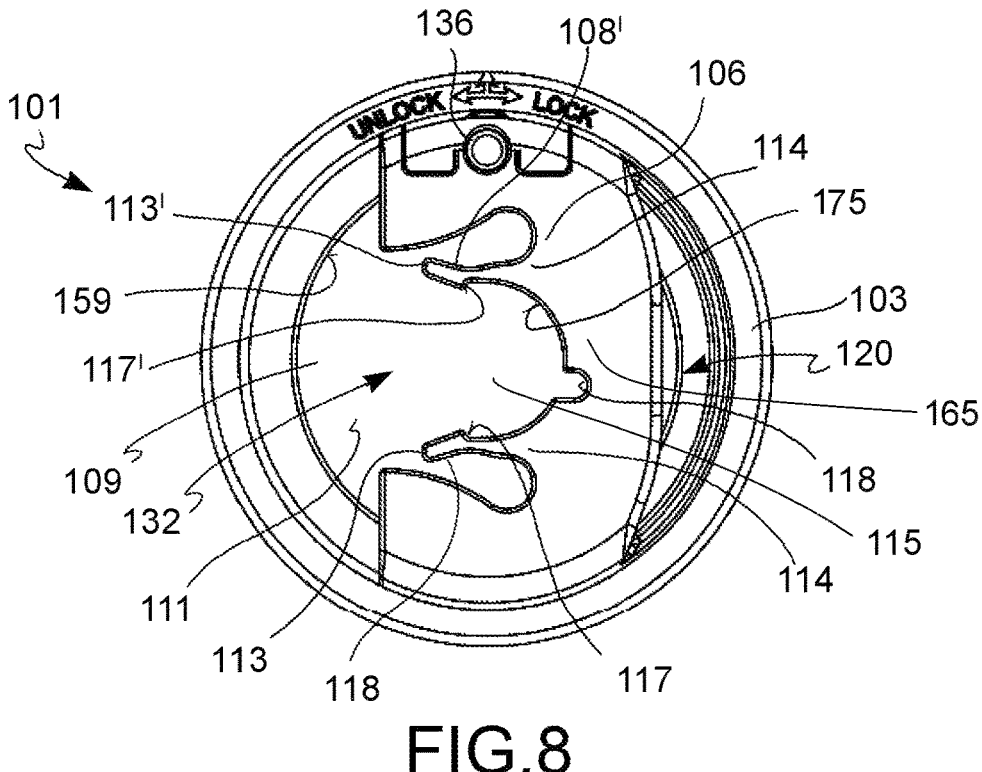
FIG. 8 shows a bottom view of the sterile adapter of FIGS. 4 and 5.
Figure 9:
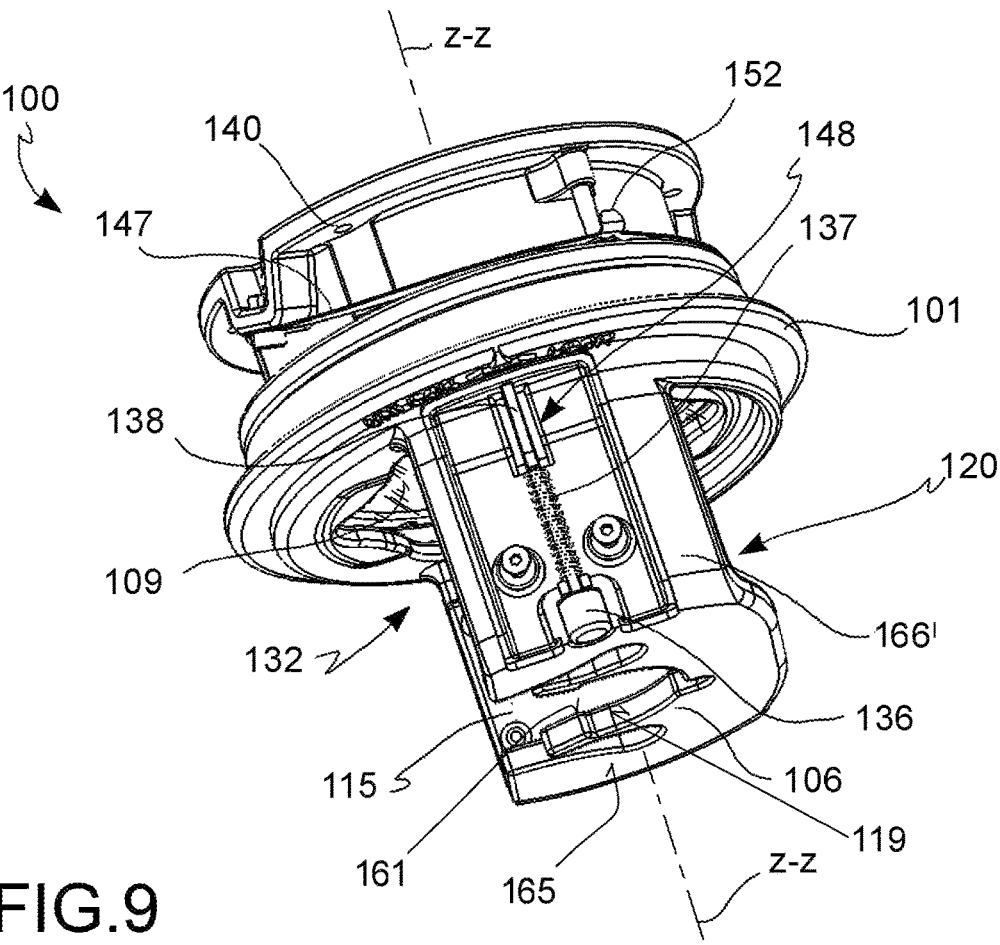
FIGS. 9 and 10 shows axonometric views of a sterile adapter, according to an embodiment, and a portion of a robotic manipulator system when in unlocked configuration and in locked configuration, respectively.
Figures 10, 11:
FIG. 11 shows a cross section of the sterile adapter and the connector when in locked configuration.
Figure 12:
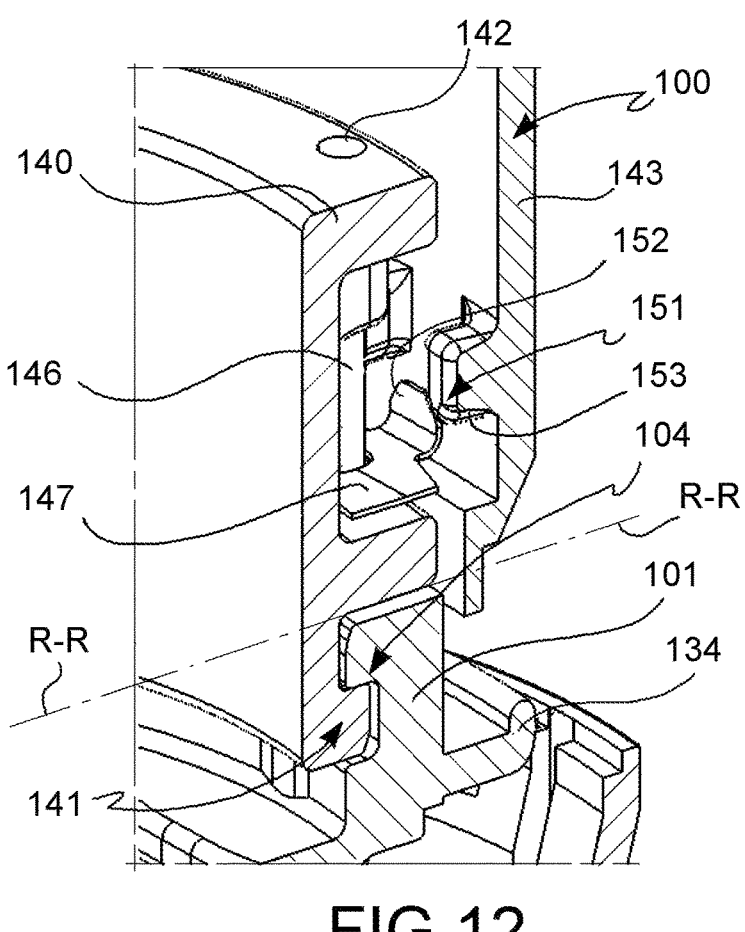
FIG. 12 shows an axonometric cross-section of a slave assembly, according to an embodiment.
Figure 13:
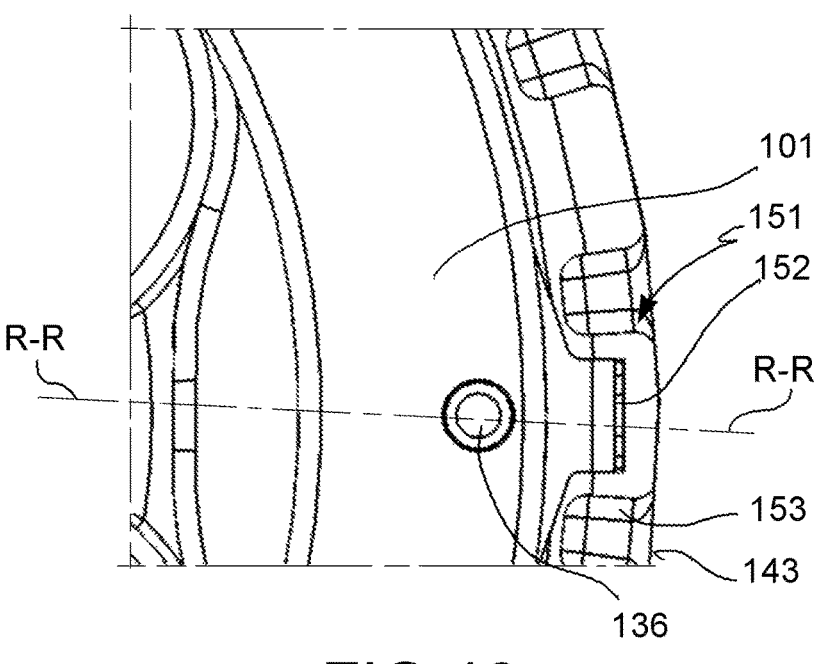
FIG. 13 shows a bottom view of the slave assembly of FIG. 12.

According to a general embodiment, it is provided a sterile adapter 101 for a robotic surgery system 102.

The sterile adapter 101 is suitable to transmit a plurality of linear displacement actions 112 and a roll action 160 from a non-sterile robotic manipulator system 105 to a sterile surgical instrument 107, the sterile surgical instrument 107 having a backend portion 123 and a shaft 121 extending from the backend portion 123.

Preferably, the terminology "surgical instrument" indicates also a "medical instrument" and the like.

Said sterile adapter 101 comprises a frame 103, for transmitting the roll action 160 from the non-sterile robotic manipulator system 105 to the sterile surgical instrument 107. The frame is preferably unsuitable to transmit the plurality of linear displacement actions 112.

Preferably, the term "roll action" used herein means an action that activates a robotic roll joint 174 or a robotic twist joint. Preferably, the sterile adapter 101 is integrally attached to the link or body that is distal or acts as output link of the robotic roll or twist joint. Such a roll action is preferably motorized, but this does not mean that the sterile adapter 101 does house motors for exerting the roll action 160. According to an embodiment, the term "roll action" may also encompass an action that activates a robotic revolving joint. According to an embodiment, said robotic manipulator system 105 comprises a roll motor 127 exerting said roll action 106.

Said frame 103 of the sterile adapter 101 comprises a proximal coupling device 104, for coupling with a non-sterile robotic manipulator system 105.

Said frame 103 of the sterile adapter 101 comprises a distal coupling device 106 for coupling with a surgical instrument 107.

Said frame 103 delimits a through opening between said proximal coupling device 104 and said distal coupling device 106.

Advantageously, said sterile adapter 101 comprises a membrane 109 fixed to said frame 103.

With additional advantage, said membrane 109 seals said through opening of the frame 103, thereby forming a distal cavity 132 between said sterile membrane 109 and said distal coupling device 106 of the frame 103 of the sterile adapter 101. Thereby, said membrane 109 is located between said proximal coupling device 104 and said distal coupling device 106. The distal cavity 132 thereby forms a pouch for receiving the surgical instrument 107.

Said membrane 109 is designed to transmit through the thickness 169 thereof the plurality of localized linear displacement actions 112 from the non-sterile robotic manipulator 105 to the sterile surgical instrument 107.

According to an embodiment, said membrane 109 has a proximal non-sterile surface 110 and a distal sterile surface 111, opposite to the proximal non-sterile surface 110, and a membrane thickness 169 between said proximal non-sterile surface 110 and said distal sterile surface 111 of the membrane 109. Thereby, the distal cavity 132 is between the distal sterile surface 111 of the membrane 109 and said distal coupling device 106. Preferably, said membrane 109 is a piece of sheet material having a substantially two-dimensional area of extent and a thickness 169 that is much smaller than the extent of the sheet material in said two dimensions.

Preferably, the term "linear displacement action" means an action that displaces an element, for example a transmission element, in a linear manner and preferably said action displaces the element along a substantially straight path. For example, said linear displacement action is a pushing action. For example, one or more pistons push on the non-sterile surface 110 of the membrane, which in turn transmits the action exerted by such one or more pistons by means of the sterile surface 111 thereof on one or more transmission elements individually aligned along a straight direction with said one or more pistons.

Preferably, the terminology "plurality of localized linear displacement actions" means that said non-sterile surface of the membrane is urged by a plurality of pistons, and the linear displacement action is directed transverse to the sterile and non-sterile surfaces 111, 110 of the membrane, so that each piston of the plurality of pistons pushes on a localized area of the non-sterile surface 110 of the membrane.

Said membrane 109 is elastically stretchable with the purpose to result elastically biased towards a substantially flat configuration thereof. According to an embodiment, said membrane 109 acts as a sterile drape. According to an embodiment, said membrane is made of flexible and stretchable sheet of transparent plastic material, for example polyethylene.

The provision of an elastically stretchable membrane allows the transmission of said plurality of localized linear displacement actions 112 through the thickness 169 of the membrane 109 by means of elastically flexing the membrane locally. Thereby volume of said distal cavity 132 is affected by the plurality of linear displacement actions 112 acting on the proximal surface 110 of said membrane 109. In particular, the membrane 109 as being stretchable, elastically deforms when stretched by said plurality of localized linear displacement actions 112, thereby modifying locally the volume of said distal cavity 132. Thereby, when in use, the membrane 109 results elastically preloaded against the distal end of at least one piston of said plurality of pistons when said at least one piston advances and pushes the non-sterile surface 110 of the membrane transversally, and preferably orthogonally, with respect to the non-sterile surface 110 of the membrane 109, so that to exert said linear displacement action 112. The material of the membrane 109 and/or the geometric parameters of the membrane 109 may be chosen to guarantee that said elastically preload against the distal end of at least one piston of said plurality of pistons is substantially negligible when in use.

Preferably, said frame 103 is substantially rigid and is more rigid than the membrane 109, in order not to stretch when said plurality of linear displacement actions 112 is exerted on said proximal non-sterile surface 110 of the membrane 109.

According to a preferred embodiment, said membrane 109 is maintained tight by the frame 103. According to an embodiment, the outer margin 173 of said membrane 109 is glued to said frame 103. According to an embodiment, the outer margin 173 of said membrane 109 is pinched to said frame body 103. According to an embodiment, the outer margin 173 of said membrane 109 is screwed to said frame body 103.

With reference to the Figures, a proximal-distal direction is generally indicated with z-z. According to an embodiment, a radial direction R-R is further defined as the direction orthogonal to and incident with said proximal-distal direction z-z. The plurality of linear displacement actions 112 are transmitted along the proximal-distal direction z-z.

According to an embodiment, the volumetric encumber of the frame 103 of the sterile adapter 101 is contained in a cylindrical geometry, preferably a discoidal geometry, having a given radius along the radial direction R-R and a predefined length along the proximal-distal direction Z-Z. According to an embodiment, the radial size of the frame 103 is maximum near or at the proximal coupling device 104 thereof.

According to an embodiment, the pushing action 112 is directed along the proximal to distal direction z-z, that is to say transversal to the membrane and preferably orthogonal to the membrane 109. Thereby, transmission of rotative action through the membrane 109 is avoided, thus reducing the risk of crumple the membrane 109.

The provision of a stretchable membrane 109 allows the transmission of a plurality of localized linear displacement actions 112, and preferably a plurality of localized pushing actions 112, across the membrane 109 and through the thickness 169 of the membrane 109, without for this reason plastically deforming the membrane 109.

Thereby, the membrane 109 is able to transmit a plurality of localized linear displacement actions 112 from said proximal non-sterile side 110 to said distal sterile side 111 of the membrane 109. According to an embodiment, the membrane 109 is also able to transmit a plurality of localized linear displacement actions 112 backwards, from said distal sterile side 111 to said proximal non-sterile side 110 of the membrane 109.

Thanks to such a membrane 109, the stretchable body of the membrane 109 itself acts as transmission element to transmit said a plurality of localized linear displacement actions 112 from the non-sterile proximal surface 110 to the sterile distal surface 111 of the membrane 109.

Conversely, the membrane 109 is unsuitable for the transmission of said roll action 160.

Thereby, it is avoided the need of providing the membrane 109 with rigid inserts acting as transmission elements. Therefore, it is also avoided the need of providing the membrane 109 with rigid plates, paddles and/or devices able to transmit a rotative action. Rotative action may be transmitted by the frame 103 of the sterile adapter 101.

The provision of such a stretchable membrane 109 allows to locally deform in an elastic manner said membrane 109 for transmitting at least one linear displacement action 112 at time through the thickness 169 of the membrane 109.

Said distal coupling device 106 comprises at least one abutment surface 161 facing said stretchable membrane 109 and thereby at least partially delimiting said distal cavity 132.

Said at least one abutment surface 161 is suitable for a portion of the surgical instrument 107 to abut thereon. Such a portion of the surgical instrument 107 that abuts against said at least one abutment surface 161 of the distal coupling device 106 of the sterile adapter 101 may be either the backend portion 123 or the shaft 121 of the surgical instrument 107.

According to a preferred embodiment, said at least one abutment surface 161 is beneath the stretchable membrane 109. In other words, said at least one abutment surface 161 in under the encumber of the membrane 109. In other words, said at least one abutment surface 161 of the distal coupling device 106 faces said membrane 109 and is contained in a prolongation along the proximal distal direction z-z of the encumber of said membrane 109. In further other words, said at least one abutment surface 161 is under the shadow of the membrane 109.

According to a preferred embodiment, said frame 103 rigidly determines the reciprocal positioning and orientation of said proximal coupling device 104 and said distal coupling device 106. Preferably, said frame 103 rigidly determines the reciprocal positioning and orientation of the proximal coupling device 104 and the lateral opening 116 of the distal coupling device 106. Preferably, the frame does not comprise hinges or movable parts or movable joints.

According to a preferred embodiment, the sterile adapter 101 comprises spacer walls 166, 166', preferably in number of two and located laterally with respect to said distal cavity 132, said spacer walls 166, 166' space the membrane 109 from the distal coupling device 106 of a predefined distance, preferably along the proximal-distal direction z-z. The spacer walls 166, 166' act as guiding walls to guide the insertion into the distal sterile cavity 132 of said backend portion 123 of the surgical instrument 107.

According to a preferred embodiment, each spacer wall 166, 166' comprises a lateral guiding surface 133, 133' delimiting partially said distal cavity 132 and adapted to mate with at least one lateral countersurface 163 of said sterile surgical instrument 107. Preferably, each of said lateral guiding surfaces 133, 133' of the distal cavity 132 of the sterile adapter 101 is substantially flat. Preferably, said at least one lateral countersurface 163 of the surgical instrument 107 is substantially flat.

According to a preferred embodiment, said distal cavity 132 includes a lateral access opening 116 designed for inserting said sterile surgical instrument 107 into the sterile adapter 101. Preferably, said lateral access opening 116 opens in a direction that is transverse to the proximal-distal direction z-z, for example it opens in the radial direction R-R.

According to a preferred embodiment, said distal cavity 132 includes a opposite lateral window 120 accessing the distal cavity 132 with the purpose of pushing said sterile surgical instrument 107 out from said distal cavity 132 of the sterile adapter 101. In other words, said sterile distal cavity 132 opens in a lateral access opening 116, or first lateral opening 116, designed for the surgical instrument 107 or at least a portion thereof to access the distal cavity 132, and opens in an opposite lateral window 120, or second lateral opening 120, designed to push the surgical instrument 107 or at least a portion thereof out from the distal cavity 132, thereby causing the surgical instrument 107 to exit said cavity 132 passing through said first opening 116, or lateral access opening 116. According to an embodiment, said lateral access opening 116 is larger than said opposite lateral window 120. Preferably, both said lateral access opening 116 and said opposite lateral window 120 are delimited by said frame 103, and preferably by said spacer walls 164, 164 of the frame 103. Preferably, said lateral access opening 116 and said opposite lateral window 120 are opposite one another in respect of said frame 103, and preferably in respect of said spacer walls 166, 166'.

According to a preferred embodiment, said distal coupling device 106 defines a distal seat 115 having a distal through opening 164 that opens distally outside of the distal cavity 132. Thereby, the frame 103 of the sterile adapter 101 comprises a distal outer surface 165 preferably located distally to said distal coupling device 106 and facing opposite in respect of said at least one abutment surface 161, and said distal through opening opens to said distal outer surface 165.

According to a preferred embodiment, said distal through opening 164 is substantially aligned with the through opening that is sealed by the stretchable membrane 109, preferably along the proximal-distal direction z-z.

According to an embodiment, said frame 103 defines an annular rim 129, or circular rim 129, forming the rim of the membrane 109. According to a preferred embodiment, said annular rim 129 holds said membrane 109. Thereby, the membrane 109 has a circumferential perimeter and preferably the membrane 109 has a circular body.

According to a preferred embodiment, said distal trough opening 164 of the sterile adapter 101 has an arched edge 175 having center of curvature aligned to the geometric center the rim 129 of the stretchable membrane 109. Thereby, said distal trough opening 164 is coaxial with the through opening of the frame 103 that is sealed by the stretchable membrane 109.

According to an embodiment, a lateral abutment wall 119 facing the distal seat 115 of the distal coupling device 106 is provided to delimit the bottom of the distal seat 115 and suitable to form an abutment surface for the surgical instrument 107 or a portion thereof, when the surgical instrument 107 is connected to the sterile adapter 101 by insertion in said distal cavity 132 through said lateral access opening 116. According to an embodiment, a centering and positioning element 118 comprising preferably a notch is realized in or near the lateral abutment wall 119 of the sterile adapter 101. According to an embodiment, said root portion 113 of the at least one elongated tongue 108 extends from said surgical instrument abutment wall 119. The provision of such a centring and positioning element 118 is provided in order to operatively connect the surgical instrument 107 to the sterile adapter 101, and said centring and positioning element 118 preferably determines the correct connection of the surgical instrument 107 to the sterile adapter 101, for example in such way to guarantee a working alignment of each of the linear actuators 126 of the robotic manipulator system 105 with respective transmission elements 124 of the backend 123 of the surgical instrument 107.

When in use, the distal coupling device 106 of the sterile adapter 101 snap-fit engages the counter-coupling device 131 of the surgical instrument 107, thereby said elongated tongues 108, 108' retain the body of the counter-coupling device 131 towards the lateral abutment wall 119 of the receiving seat 115 of the sterile adapter 101.

When the sterile adapter 101 rotates and carries a surgical instrument 107, it rotates about an axis z-z that is coaxial with the shaft 121 of the surgical instrument 107, which therefore pivots and does not revolute.

According to an embodiment, said membrane 109 is fixed to said annular rim 129, and said annular rim 129 is made of said frame body 103. According to an embodiment, the circular rim 129 comprises an inner edge 156 facing said membrane 109 and an outer annular edge. Said inner edge 156 may be annular in shape or may have projections 158 protruding radially inwards, and said projections 158 do not partition the membrane 109 so that to avoid discontinuities in the structure and in the dynamic behaviour of the membrane 109. According to an embodiment, said inner edge 156 of the annular rim 129 facing the membrane 109 describes a single rim perimeter line 159. According to an embodiment, said annular rim 129 has a constant extension in the radial direction R-R.

According to a preferred embodiment, said membrane 109 is in single piece, preferably in a single flat piece or sheet of elastic material. In other words, the membrane is made monoblock. Thereby, the number of components of the sterile adapter 101 is reduced. Moreover, the risk of disengagement of parts of the membrane 109 is avoided.

According to a preferred embodiment, said membrane 109 forms a continuous surface. According to a preferred embodiment, said membrane 109 forms two opposite continuous surfaces 110, 111. According to an embodiment, the terminology "continuous surface" means that the structural and dynamic behaviour of the membrane 109 is continuous along the entire body of the membrane 109, avoiding providing stiffening portions and/or stiffening plates, as well as through holes for the passage of an actuator and/or a transmission device. According to an embodiment, the terminology "continuous surface" means that the membrane 109 does not comprises discontinuities. For example, said discontinuities are holes and/or cuffs. Such discontinuities, for example cuffs, requires a forming process of manufacturing, for example thermoforming or the like, that plastically deforms the membrane 109 during manufacturing, creating said discontinuities.

According to a preferred embodiment, said membrane 109 lies in plane, preferably orthogonal to the proximal-distal direction Z-Z. According to a preferred embodiment, said membrane 109 forms planar surfaces 110, 111 and it is contained within the volumetric encumber of the frame body 103 of the sterile adapter 101. According to an embodiment, the membrane 109 extends transversally and/or orthogonal to the proximal-distal direction Z-Z. According to an embodiment, said membrane 109 does not have folds. According to an embodiment, said membrane 109 has constant thickness 169, for example comprised between 2 to 6 millimetres. According to an embodiment, said membrane 109 avoids comprising pockets for hosting an actuator and/or a transmission device or the like. According to an embodiment, said membrane 109 avoids comprising stiffened portions, for example comprising paddles, for transmitting a rotational movement through the membrane 109.

According to a preferred embodiment, said distal coupling device 106 of the sterile adapter 101 is designed to snap-fit engage with a portion of a surgical instrument 107, and preferably with a counter-coupling portion 131 of the surgical instrument 107.

According to a preferred embodiment, said distal coupling device 106 of the sterile adapter 101 comprises at least one elongated elastic tongue 108, 108' protruding cantilevered and thereby forming an end 113, preferably a free end 113, and a root portion 114.

According to an embodiment, said distal coupling device 106 of the sterile adapter 101 comprises a distal seat 115 delimited at least partially by said at least one elongated tongue 108, 108', wherein said receiving seat 115 comprises a lateral access mouth facing towards the same engaging direction 128 of the lateral access opening 116 of the distal cavity 132. According to an embodiment, said at least one elongated tongue 108, 108' is elastically biased to reduce the width of said access mouth 116 of the receiving seat 115 to form a snap-fit engagement with the surgical instrument 107.

According to a preferred embodiment, said two elongated tongues 108 and 108' are provided delimiting the access mouth there between to access the distal seat 115, and preferably delimiting the distal seat 115.

According to a preferred embodiment, the at least one elongated tongue 108, 108' is substantially parallel to the membrane 109. In other words, the at least one elongated tongue 108, 108' extend transversally to said proximal-distal direction z-z.

According to an embodiment, said at least one elongated tongue 108, 108', and preferably each of said elongated tongues 108 and 108', comprises an abutment portion or retaining portion 117, 117' facing said distal seat 115. Thanks to said retaining portions 117, 117' of the elongated tongue 108, 108' suitable for snap-fit engaging the surgical instrument 107, a constraining action is provided constraining the surgical instrument 107 within the distal seat 115 and preferably against said lateral abutment wall 119. According to an embodiment, said retaining portions 117, 117' of the elongated tongues 108, 108' face said lateral abutment surface 119 of the distal seat 115. According to an embodiment, said retaining portions 117, 117' are located on protrusions protruding inwardly towards the receiving seat 115 so that to make the access mouth 116 to the seat 115 narrower.

According to an embodiment, said access mouth of the distal seat 115 for the surgical instrument 107 is open in an engagement direction 128 transversal to the proximal-distal direction z-z so that the surgical instrument 107 can be connected to, and disconnected from, said sterile adapter 101 with a transversal movement along an engagement direction 128. According to an embodiment, said engagement direction is parallel to or coincident with said radial direction R-R.

Thereby, the surgical instrument 107 can be connected to, and disconnected from, said sterile adapter 101 with a lateral displacement movement. In other words, the engagement direction 128 is transversal to the proximal-distal direction z-z. Thereby, the surgical instrument 107 can be disconnected from said sterile adapter 101 moving away from a patient anatomy and/or from an operatory bed. Thereby, the surgical instrument 107 can be connected to said sterile adapter 101 along said transverse engagement direction 128.

According to an embodiment, said frame body 103 of the sterile adapter 101 delimits, between the membrane 109 and the distal coupling portion 106, a distal cavity 132 designed to receive at least a portion of said backend portion 123 of the surgical instrument 107. According to an embodiment, said housing 132 is open form the same side of the access mouth of the distal seat 115, so that when the counter-coupling portion 131 of the surgical instrument 107 is detachably connected with the coupling device 106 of the sterile adapter 101, the backend portion 123 is received within said distal cavity 132.

The linear displacement actions 112 locally exerted on said proximal surface 110 of the membrane 109 determines a local stretch of the membrane 109 thereby transferring through the thickness 169 of the membrane 109 such linear displacement actions 112 to the backend 123 of the surgical instrument 107, which comprises transmission elements 124, for example rods, aligned with the linear actuators 126 of the robotic motorized manipulator system 105.

According to an embodiment, said frame 103 delimits at least one ejection window 120, suitable to permit the access to a portion of the surgical instrument 107 in order to push it for the removal from said distal cavity 106 of the sterile adapter 101. Thereby, a quick disengagement action is allowed. Thereby, the backend portion 123 of the surgical instrument 107 also exits the housing 132. For example, a hand pushing action 122 trough said ejection window 120 can disengage the surgical instrument 107 in a direction pointing away from the patient anatomy.

According to an embodiment, said window 120 faces opposite in respect of said access mouth 116. According to an embodiment, said window 120 faces opposite in respect of the access side of the housing 123.

According to an embodiment, said proximal coupling device 104 comprises threaded elements in order to be screwed to said robotic manipulator system 105.

According to a preferred embodiment, said proximal coupling device 104 defines a circular shape defining an axial-symmetrical coupling body.

The provision of such an annular rim 129 allows the sterile adapter 101 to pivot about an axis, preferably parallel to said proximal-distal direction Z-Z, without for this reason to tear or crumble the membrane 109. Tearing and crumbling of the membrane 109 will result in a loss of sterility of the surgical instrument 107.

According to an embodiment, said proximal coupling device 104 is designed to form a bayonet type coupling with a portion of the robot manipulator system 105. According to an embodiment, said proximal coupling device 104 comprises undercuts elements, undercut in respect of said proximal-distal direction Z-Z to couple with the robot manipulator system 105.

According to an embodiment, said frame body 103 of the sterile adapter 101 comprises a skirt 134 of enlarged radial dimension near the proximal end thereof.

According to an embodiment, said frame 103 of the sterile adapter 101 comprises said proximal coupling device 104, said distal coupling device 106, spacer walls 133, 133' delimiting at least partially said housing 132 and said window 120 open in the radial direction R-R at opposite sides of the spacer walls 113, 113'.

According to an embodiment, said sterile adapter 101 comprises a flag device 135 flagging when the sterile adapter 101 is coupled to the robotic manipulator system 105. According to an embodiment, said flagging device 135 comprises a flagging pin 138 comprising a distal pin end 136, suitable for protruding cantilevered from the frame body 103 of the sterile adapter 101 when the sterile adapter 101 is coupled to the robotic manipulator system 105, thereby flagging the event of successful coupling. According to an embodiment, said flagging device 135 comprises an elastic device 137 biasing the flagging pin 138 proximally, for example so that to bias the distal pin end 136 to be flush with the distal portion of the sterile adapter 101. When the sterile adapter 101 is coupled to the robotic manipulator system 105, the flagging pin 138 abuts against an abutment element 139 of the robotic manipulator system 105 against the biasing action exerted by the elastic device 137 thereby causing the distal pin end 136 of the flagging pin 138 to protrude distally from the sterile adapter 101. A removable panel 150 may be provided for protecting the flagging device 135.

According to an embodiment, the distal pin end 136 is made in separate piece in respect of the flagging pin 138. According to an embodiment, said elastic device 137 of the connector 140 comprises an axial spring fitted around the flagging pin 138. According to an embodiment, said flagging device 135 further comprises a flagging pin housing 148 receiving at least a portion of the flagging pin 138. According to an embodiment, said flagging pin housing 148 receiving at least a portion of the flagging pin 138 forms a through hole extending substantially along the proximal-distal direction Z-Z through a sidewall 133' of the frame body 103 of the sterile adapter 101. Abutment surfaces may be provided in said flagging pin housing 148 to stop the displacement of the flagging pin 138 by means of cooperation with counter-abutment surfaces that may be provided to the pin 138. For example, the pin 138 may have a flared portion suitable to abut against a surface of the housing 148. According to an embodiment, the flagging pin 138 comprises an inclined segment 149 forming an angle with said proximal-distal direction Z-Z and suitable to abut against a surface of the housing 148.

According to an embodiment, it is provided a mechanism that impedes to remove the sterile adapter from the connector when the surgical instrument is coupled to the sterile adapter.

According to an embodiment, the sterile adapter 101 transmits a plurality of linear actuation actions 112 and a roll action 160 from the non-sterile robotic manipulator system 105 to the sterile surgical instrument 107 having a backend portion 123 and a shaft 121 extending from said backend portion 123, the sterile adapter 101 comprising said frame 103 transmitting the roll action 160 from the non-sterile robotic manipulator system 105 to the sterile surgical instrument 107, the frame 103 comprising said proximal coupling device 104, coupling with the non-sterile robotic manipulator system 105, and said distal coupling device 106, coupling with the sterile surgical instrument 107, wherein said frame 103 delimits a through opening between said proximal coupling device 106 and said distal coupling device 106; and wherein said sterile adapter 101 further comprising said membrane 109 fixed to said frame 103, transmitting through the thickness 169 thereof the plurality of localized linear actuation actions 112 from the non-sterile robotic manipulator 105 to the sterile surgical instrument 107; and wherein said membrane 109 is elastically stretchable resulting elastically biased towards a substantially flat configuration thereof; and wherein said stretchable membrane 109 seals said through opening forming a distal cavity 132 between said stretchable membrane 109 and said distal coupling device 106; and wherein said distal cavity 132 receiving at least a portion of the backend 123 of the sterile surgical instrument 107; and wherein said distal coupling device 106 comprises at least one abutment surface 161 facing said stretchable membrane 109 and thereby at least partially delimiting said distal cavity 132, said at least one abutment surface 161 being suitable for a portion of the surgical instrument 107 to abut thereon so that the surgical instrument 107 abuts against said at least one abutment surface 161.

According to an embodiment, said membrane 109 has shape of a disc.

According to an embodiment, said membrane 109 is integrally mounted with said frame 103.

According to an embodiment, said proximal coupling device 104 and said distal coupling device 106 of said frame 103 are made in single piece.

According to a general embodiment, a slave assembly 100 for a robotic surgery system 102 comprises at least one sterile adapter 101 according to any one of the embodiments described above.

Said slave assembly 100 comprises at least one connector 140 coupled to the proximal coupling device 104 of the sterile adapter 101. According to an embodiment, said connector 140 comprises a distal counter-coupling device 141 suitable to form a connection with said proximal coupling device 104 of the sterile adapter 101. According to an embodiment, said distal counter-coupling device 141 of the connection 140 and the proximal coupling portion 104 of the sterile adapter 101 form a bayonet type engagement.

According to an embodiment, said slave assembly 100 comprises at least one robotic manipulator system 105 according to any one of the embodiments described above.

According to an embodiment, said slave assembly 100 comprises at least one surgical instrument 107 according to any one of the embodiments described above, and comprising a backend portion 123 and a shaft 121 extending from said backend portion 123. According to a preferred embodiment, said lateral access opening 116 and said opposite lateral window 120 of the sterile adapter 101 are opposite one another in respect of said backend portion 123 of the surgical instrument 107.

According to an embodiment, said slave robot assembly 100 for a robotic surgery system 102 comprises said non-sterile robotic manipulator system 105, said sterile surgical instrument 107 having said backend portion 123 and said shaft 121 extending from said backend portion 123, and said sterile adapter 101, suitable to transmit a plurality of linear actuation actions 112 and a roll action 160 from said non-sterile robotic manipulator system 105 to said sterile surgical instrument 107; wherein said sterile adapter 101 comprises said frame 103 transmitting the roll action 160 from the non-sterile robotic manipulator system 105 to the sterile surgical instrument 107, and wherein said frame 103 comprises said proximal coupling device 104, coupled with the non-sterile robotic manipulator system 105, and said distal coupling device 106, coupled with the sterile surgical instrument 107; and wherein said frame 103 delimits a through opening between said proximal coupling device 106 and said distal coupling device 106; and wherein said sterile adapter 101 comprises said membrane 109 fixed to said frame 103, transmitting through the thickness 169 thereof the plurality of localized linear actuation actions 112 from the non-sterile robotic manipulator 105 to the sterile surgical instrument 107; and wherein said membrane 109 is elastically stretchable resulting elastically biased towards a substantially flat configuration thereof; and wherein said stretchable membrane 109 seals said through opening forming said distal cavity 132 between said stretchable membrane 109 and said distal coupling device 106; said distal cavity 132 receives at least a portion of the backend 123 of the sterile surgical instrument 107; said distal coupling device 106 comprises at least one abutment surface 161 facing said stretchable membrane 109 and thereby at least partially delimiting said distal cavity 132; and wherein the surgical instrument 107 abuts against said at least one abutment surface 161.

According to an embodiment, the geometric center of the membrane 109 is aligned with the shaft 121 of the sterile surgical instrument 107.

According to an embodiment, the plurality of localized linear actuation actions 112 are directed orthogonally to a proximal surface 110 of the membrane 109.

According to an embodiment, the sterile adapter 101 rotates together with the sterile surgical instrument 107.

According to an embodiment, the non-sterile robotic manipulator system 105 comprises a plurality of linear actuators 126 and the membrane 109 is elastically preloaded against the distal end of at least one of said plurality of linear actuators 126 when said at least one linear actuator 126 of said plurality of linear actuators 126 advances distally.

According to an embodiment, the plurality of localized linear actuation actions 112 are aligned with the shaft 121 of the surgical instrument 107.

According to an embodiment, the plurality of localized linear actuation actions 112 exert a pushing action to load the surgical instrument 107 against said at least one abutment surface 161.

According to an embodiment, said sterile adapter 101 is detachably coupled with said non-sterile robotic manipulator system 105 and/or wherein said surgical instrument 107 is detachably coupled with said sterile adapter 101.

According to an embodiment, said slave robot assembly 100 comprises at least a rotary joint 174 transmitting said roll action 160 to the surgical instrument 107 by means of said frame 103 of the sterile adapter 101.

According to an embodiment, said slave assembly 100 comprises at least one sterile drape 144 covering at least a portion of said robotic slave assembly 100 forming a sterile barrier suitable to impede contamination of the surgical instrument 107.

Advantageously, said sterile drape 144 cooperates with said membrane 109 of the sterile adapter 101 to form a sterile barrier.

According to a preferred embodiment, said sterile adapter 101 is disposable. According to a preferred embodiment, said sterile adapter 101 is designed to be a single-use sterile adapter 101.

According to an embodiment, said connector 140 comprises proximal connecting means 142 for connecting the connector 140 to the robotic manipulator system 105.

According to an embodiment, said slave assembly 100 comprises a protective case 143 enclosing at least a portion of the robotic motorized manipulator system 105 and said connector 140.

According to an embodiment, said connector 140 comprises a proximal flagging device 145 cooperating with the flagging device 135 of the sterile adapter 101 to flag when the sterile adapter 101 is coupled with the non-sterile connector 140. According to an embodiment, said proximal flagging device 145 comprises said abutment portion 139 for a proximal end of the flagging pin 138 of the flagging device 135. According to an embodiment, said proximal flagging device 145 comprises an elastic element 147 biasing said abutment portion 139, for example the distal end of an abutting pin 146, distally towards the flagging pin 138 of the flagging device 135 of the sterile adapter 101. Guiding elements, such as walls of a cavity, may be provided to align the flagging pin 138 and the abutment pin 146 along the proximal-distal direction Z-Z and to guide the displacement thereof in the proximal-distal direction Z-Z.

According to an embodiment, said elastic element 147 of the connector 140 comprises a leaf spring secured to a portion of the connector 140. According to an embodiment, said elastic element 147 is form-fitted with said abutment pin 146 in order to not to slide along the body of said abutment pin 146.

According to an embodiment, said connector 140 has substantially an annular shape suitable to pivot about an axis, preferably coinciding with said proximal-distal direction Z-Z. Thereby, the proximal connection portion 142 of the connector 140 is suitable to transmit rotative action 160 to the connector 140 and the distal counter-coupling device 141 of the connector is suitable to transmit rotative action to the sterile adapter 101 comprising the membrane 109. This way, the connector 140, the sterile adapter 101 and the surgical instrument 107 can integrally pivot in respect of the protective case 143. In other words, the connector 140, the sterile adapter 101 and the surgical instrument 107 can pivot all together as a single piece in respect of the protective case 143, when actuated by a rotative actuator 127.

According to an embodiment, said connector 140 has substantially an annular shape that contours an inner cavity 154 suitable for receiving said linear actuators 126 of the robotic manipulator system 105. According to an embodiment, said inner cavity 154 is a through hole extending in the proximal-distal direction Z-Z. Thus, said shaft 121 of the surgical instrument 107 is integral with the backend portion 123 so that no relative pivoting action is allowed. Thereby, no motors are needed downstream the membrane 109 allowing the miniaturization of the surgical instrument and particularly of the wrist 122.

According to an embodiment, said inner cavity 154 of the connector 140 is delimited distally by the membrane 109 of the sterile adapter 101. In other words, the housing 132 of the sterile adapter 101 and the inner cavity 154 of the connector 140 are partitioned by means of interposition of said stretchable membrane 109. Thereby, linear actuators of the manipulator system 105 and transmission rods of the backend 123 received in said inner cavity 154 and in said housing, respectively, can exchange pushing actions 112 through the body of the stretchable membrane 109.

According to an embodiment, said elastic device 147 of the connector 140 may form a part of an anti-rotation system 151 designed to avoid relative rotation of the connector 140 and the sterile adapter 101 during the coupling of the sterile adapter 101 to the connector 140.

According to an embodiment, said anti-rotation system 151 comprises a radially cantilevered element 152, radially protruding away to the rotation axis of the connector 140 and/or of the adapter 101, to abut against a radially inward block tooth 153 of the protective case 143. According to an embodiment, the elastic device 147 of the connector 140 biases distally the radially cantilevered element 152.

When the abutting pin 146 of the connector 140 engages the flagging pin 138 of the sterile adapter 101 biasing distally the distal pin end 136 of the flagging pin 136, the radially cantilevered element 152 of the anti-rotation system 151 is moved distally so that it avoids abutting against the block tooth 153, thereby allowing relative pivot of both the connector 140 and the sterile adapter 101 in respect of the protective case 143 of the slave robot assembly 100.

By means of pressing the distal pin end 136 of the flagging pin 138 towards the proximal direction, it is possible to unlock, for example unscrew, the sterile adapter 101 from the connector 140. Preferably, an anti-removal mechanism 176 is provided in order to avoid unlocking the sterile adapter 101 from the connector 140 when a surgical instrument 107 is received within said cavity 132 of the sterile adapter 101. Preferably, said anti-removal mechanism 176 is comprises an abutment surface integral with the distal pin end 136 of the flagging pin 138 and that faces the cavity 132 of the sterile adapter 101, said abutment surface of the anti-removal mechanism 176 is suitable to abut against a portion of the surgical instrument thereby preventing the distal end 136 of the flagging pin 138 to be pressed proximally. When the surgical instrument is out from the cavity 132, then the flagging pin 138 is free to move distally when pressed onto said flagging pin end 136, thus disengaging the sterile adapter 101 from the connector 140. Thereby the pin distal end 136 acts as a unlock button for the sterile adapter 101 and the anti-removal mechanism 176 acts a safety device preventing to detach the sterile adapter 101 from the robotic slave assembly 100 while the surgical instrument 107 is received within the housing 132. The abutment surface of the anti-removal mechanism 176 may also be provided not integrally formed with the distal pin end 136 of the flagging pin 138.

According to a general embodiment, a robotic surgery system 102 comprises at least one sterile adapter 101 according to any of the embodiments described above.

The robotic surgery system 102 may comprise also at least one master console 130 controlling said slave robot assembly 100.

The robotic surgery system 102 may comprise any of the features or combination thereof described above in relation of the robotic surgery system 102.

According to a preferred embodiment, said robotic surgery system 102 comprises at least one slave assembly 100 according to any of the embodiments described above.

According to a preferred embodiment, said robotic surgery system 102 comprises at least a pair of robotic motorized manipulator systems 105 both connected to a single robotic positioning arm link 155.

According to a preferred embodiment, said proximal non-sterile surface 110 of the membrane 109 of the sterile adapter 101 faces said non-sterile robotic manipulator system 105, and said sterile surface 111 of the membrane 109 faces said surgical instrument 107.

Advantageously, said robotic surgery system 102 comprises at least a rotary joint 174 or roll joint 174 or twist joint 174. Preferably, said at least one rotary joint 174 is a twist joint suitable to transmit said roll action 160 by means of the frame 103 of the sterile adapter 101.

According to a preferred embodiment, said sterile adapter 101 is integrally connectable to said roll joint 174 in order to rotate with it.

When the sterile adapter 101 rotates and carries a surgical instrument 107, it rotates about an axis z-z that is coaxial with the shaft 121 of the surgical instrument 107, which therefore pivots and does not revolute, forming such a roll joint 174 transmitting said roll action 160.

According to a preferred embodiment, said plurality of localized pushing actions 112 urge said sterile surgical instrument 107 against said at least one abutment surface 161 of the sterile adapter 101.

According to a preferred embodiment, said sterile surgical instrument 107 comprises at least one distal counter-abutment surface 162 abutting against said at least one abutment surface 161 of the sterile adapter 101.

According to a preferred embodiment, said robotic surgery system 102 comprises an anti-rotation system 151, designed to avoid relative rotation of the connector 140 and the sterile adapter 101 during the coupling of the sterile adapter 101 to the connector 140; and/or wherein According to a preferred embodiment, said anti-rotation system 151 comprises a radially cantilevered element 152, radially protruding away to the rotation axis of the connector 140 and/or of the adapter 101, to abut against a radially inward block tooth 153 of a protective case 143 of robotic surgery system 100.

731. According to a preferred embodiment, said robotic surgery system 102 further comprises at least a surgical instrument 107 comprising a instrument shaft 121 extending substantially along the proximal-distal direction Z-Z and having a proximal end 171 and a distal end 172, a surgical end effector 122 at the distal end 172 of the shaft 121, a backend portion 123 connected to the proximal end 171 of the shaft 121, a counter-coupling device 131 located near or at the proximal end 171 of the shaft 121 suitable for forming a snap-fit engagement with said distal coupling device 106 of the sterile adapter 101.

According to a preferred embodiment, in order to transmit said pushing action 112, the proximal surface 110 of the membrane 109 comes into contact with a distal surface of a linear actuator 126 of the robotic manipulator system 105, and as the linear actuator 126 advances distally, the body of the membrane 109 stretches so that the distal surface 111 of the membrane 109 comes into contact with a proximal surface of a transmission rod 124 of the backend portion 123 of the surgical instrument 107.

According to a preferred embodiment, said counter-coupling device 131 is located near or at the proximal end 171 of the shaft 121 of the surgical instrument 107.

According to a preferred embodiment, said counter-coupling device 131 of the surgical instrument 107 comprises body having a tapered shape, for example a frusto-conical shape, in order to form-fit the size of the distal seat 115. According to a preferred embodiment, the body of said counter coupling device 131 tapers towards the distal end 172 of the shaft 121.

The provision of a tapered body of said counter-coupling device 131 of the surgical instrument 107 allows to form-fit the receiving seat 115 of the sterile adapter 101 when the backend portion 123 is pushed distally as effect of the pushing action 112 exerted on the transmission rods 124 of the backend portion 123 of the surgical instrument 107.

According to an embodiment, said surgical instrument 107 comprises a instrument shaft 121 extending substantially along the proximal-distal direction z-z and having a proximal end 171 and a distal end 172, a surgical end effector 122 at the distal end of the shaft 121 and a backend portion 123 at or near the proximal end of the shaft 121.

The shaft 121 preferably extend along a direction that is aligned and preferably coaxial with both the distal opening 115 of the coupling device 106 of the sterile adapter 101 and the opening of the frame 103 of the sterile adapter 101 that is sealed by the membrane 109. In other words, the shaft 121 is designed for not to revolute, but instead to pivot or roll around its axis of longitudinal development when the sterile adapter 101 rolls or twists in respect of the protective case 143 and/or a reference point of the motorized manipulator system 105 or of the robotic surgery system 102.

According to an embodiment, the backend portion 123 is suitable to receive the pushing action 112 transmitted through and across the membrane 109. According to an embodiment, the backend portion 123 comprises a plurality of transmission rods 124 or the like, suitable to be pushed in order to actuate at least one actuation cable 125 of the surgical instrument to in turn actuate the end effector 122, for example a surgical wrist 122. According to an embodiment, said transmission rods 124 are linearly displaceable.

According to an embodiment, the backend portion 123 houses said transmission rods 124 and a proximal portion of said actuation cables 125 or tendons 125.

According to an embodiment, in order to transmit said plurality of localized linear displacement actions 112, the proximal non-sterile surface 110 of the membrane 109 comes into contact with a distal portion 168 of a linear actuator 126 of the robotic manipulator system 105, and as the linear actuator 126 advances distally, the body of the membrane 109 stretches so that the distal surface 111 of the membrane 109 comes into contact with a proximal portion 167 of a transmission element 124 of the backend portion 123 of the surgical instrument 107. According to an embodiment, said linear actuator 126 is suitable to exert a pushing action 112.

According to an embodiment, said robotic manipulator system 105 is a portion of a slave assembly 100 of said robotic surgery system 102 and is suitable to be controlled by means of a master console 130 of said robotic surgery system 102.

According to an embodiment, said robotic manipulator system 105 comprises a plurality of motorized actuators, able to actuate linear actuators 126 for exerting said pushing action 112, and preferably, said linear actuators 126 are linearly displaceable along the proximal-distal direction z-z.

According to an embodiment, said robotic manipulator system 105 further comprises a rotative actuator 127 suitable to make the sterile adapter 101 to pivot around a rotation axis, preferably parallel to the proximal-distal direction z-z, and preferably coinciding with said proximal-distal direction z-z.

A method of transmission of a roll action 160 and of a plurality localized linear displacement actions 112 across a sterile barrier will be described in the following.

The method of transmission of a roll action 160 and of a plurality localized linear displacement actions 112 across a sterile barrier comprises the following steps:

providing a sterile adapter 101 comprising a frame 103 and a stretchable membrane 109 fixed to said frame 103, the stretchable membrane 109 being part of the sterile barrier;

transmitting said roll action 160 by means of the frame 103 of the sterile adapter 101;

transmitting said plurality of localized linear displacement actions 112 by means of the membrane 109, through the thickness 169 thereof.

Preferably, said roll action 160 and said plurality of localized linear displacement actions 112 are exerted by at least one motorized manipulator system 105. Motors of the at least one motorized manipulator system 105 may be housed within a motor box or motor housing 170 preferably covered by a protective case 143. The motors of the motorized manipulator system 105 are preferably upstream the sterile adapter. Distally to the sterile adapter, a surgical instrument may be connected, and the surgical instrument may comprise a shaft having at or near the distal end thereof an articulated end effector comprising a pitch, a yaw and a grip degrees of freedom, which are all actuated by the linear displacement actions transmitted through the membrane 109 of the sterile adapter, which in turn actuates actuation cables connected to the articulated end effector through the shaft.

According to a preferred mode of operation, the sterile adapter 101 according to any of the embodiments described above is designed to perform the method steps mentioned above. Thereby, the method comprises the step of providing a sterile adapter 101 according to any of the embodiment described above.

According to a preferred mode of operation, the slave assembly 100 according to any of the embodiments described above is designed to perform the method steps mentioned above. Thereby, the method comprises the step of providing a slave assembly 100 according to any of the embodiment described above.

According to a preferred mode of operation, the robotic surgery system 102 according to any of the embodiments described above is designed to perform the method steps mentioned above. Thereby, the method comprises the step of providing the robotic surgery system 102 according to any of the embodiment described above.

Thanks to the features described above provided either together or disjointly in particular embodiments, it is allowed to respond to the above-mentioned needs providing the above cited advantages, and in particular:

- transmission of roll action and a plurality of localized linear displacement actions may be achieved by means of the sterile adapter connected to a rotary joint of a robotic surgery system;
- the roll action is transmitted by the rigid frame 103 of the sterile adapter;
- the plurality of localized linear displacement actions are transmitted by a stretchable membrane 109 through the thickness 169 thereof;
- the shaft of a surgical instrument may pivot around its own axis of longitudinal development, while avoiding providing motors in the surgical instrument 107;
- the surgical instrument 107 is detachably connectable to the sterile adapter 101 and remains within a sterile operatory field;
- the localized linear displacement actions 112 actuate the degrees of freedom of the end effector, such as s a wrist device, at the distal end of the shaft of the surgical instrument;
- the body of the membrane 109 is uninterrupted and able to transmit a plurality of localized linear displacement actions 112;
- the membrane is unsuitable to transmit the roll action;
- the membrane rotates (i.e. rolls) together with the frame of the adapter and together with the surgical instrument when the roll motor 127 generates the roll action to the frame of the sterile adapter;
- the membrane is devoid of pockets for individually receive a respective single linear actuator;

the "area of the membrane"-to-"volume of the frame"-ratio is optimized, the sterile adapter provides a compact yet highly functional solution;

the same membrane transmits at least a pair of agonist and antagonist actuation actions to the surgical instrument; in other words, the plurality of linear actuators may comprise agonist and antagonist actuators both acting on the same membrane;

the same membrane as per receiving a plurality of linear displacement actions generated by a plurality of linear actuators orthogonally to the proximal and distal surface of the membrane is subject to minor local deformation with respect to the known solutions having individual pockets for individually receiving a respective single linear actuator and that may result in a more robust solution;

the same membrane as per receiving a plurality of linear displacement actions allows for a simpler manufacturing and assembly with respect to known solutions;

the membrane is elastically preloaded against the distal end of at least one linear actuator, such as a piston, when the linear actuator advances distally with the purpose of transmitting a linear displacement action to the backend of a surgical instrument housed within the cavity of the sterile adapter;

the roll motor 127 providing a roll degree of freedom to the surgical instrument is upstream the linear actuators of the motorized manipulator, so that the linear actuators rotate or roll together with the sterile adapter;

the geometric centre of the membrane is aligned with the shaft of the surgical instrument;

the surgical instrument in inserted laterally into the sterile adapter;

the cavity of the sterile adapter receiving the instrument forms a pouch opened laterally, said pouch being deformed by the linear displacement actions acting orthogonally to the membrane;

the surgical instrument can be inserted into the sterile adapter after having connected the sterile adapter to the robotic manipulator;

the sterile adapter defines a portion of the sterile barrier and a seat for the surgical instrument, wherein the seat for the surgical instrument protrudes distally from the sterile barrier.

Those skilled in art may make many changes and adaptations to the embodiments described above or may replace elements with others, which are functionally equivalent in order to satisfy contingent needs without however departing from the scope of the appended claims.

LIST OF REFERENCES

- 100 Slave robot assembly, or slave assembly
- 101 Sterile adapter or adapter
- 102 Robotic surgery system
- 103 Frame of the sterile adapter
- 104 Proximal coupling device of the sterile adapter
- 105 Robotic manipulator system, or motorized manipulator system
- 106 Distal coupling device of the sterile adapter
- 107 Surgical instrument
- 108, 108' Elongated tongue
- 109 Stretchable membrane of the sterile adapter
- 110 Proximal non-sterile surface of the membrane
- 111 Distal sterile surface of the membrane
- 112 Localized linear displacement action 113, 113' End of the elongated tongue
114 Root portion of the elongated tongue
115 Distal seat of sterile adapter
116 Lateral access opening
117, 117' Retaining or abutment portion of the elongated tongue
118 Centring element
119 Lateral abutment wall of the distal seat
120 Second opening of the sterile adapter
121 Shaft of surgical instrument
122 End effector, or wrist, of the surgical instrument
123 Backend, or backend portion, of the surgical instrument
124 Transmission element, or rod, of the backend
125 Actuation cable, or tendon, of the surgical instrument
126 Linear actuator of the robotic manipulator system
127 Roll motor of the motorized manipulator system
128 Engagement direction
129 Annular rim of the sterile adapter, or circular rim
130 Master console of the robotic surgery system
131 Counter-coupling portion of the surgical instrument
132 Distal cavity of the sterile adapter
133, 133' Lateral guiding surface of the sterile adapter
134 Skirt of the sterile adapter
135 Flag device of the sterile adapter
136 Distal pin end of the flagging pin
137 Elastic element of the flagging device
138 Flagging pin of the flagging device
139 Abutment portion for the flagging pin
140 Connector, or annular connector of the slave assembly
141 Distal counter-coupling device of the connector
142 Proximal connection portion of the connector
143 Protective case of the slave assembly
144 Sterile drape of the robotic slave assembly
145 Proximal flagging device of the connector
146 Abutment pin of the connector
147 Elastic device of the connector
148 Flagging pin housing of the sterile adapter
149 Inclined segment of the flagging pin
150 Removable panel
151 Anti-rotation system
152 Radially cantilevered element of the anti-rotation system
153 Blocking tooth of the anti-rotation system
154 Inner cavity of the connector
155 Robotic arm link
156 Inner edge of the annular rim
158 Projections of the annular rim
159 Perimeter of the annular rim
160 Roll action
161 Abutment surface of the sterile adapter
162 Counter abutment surface of the surgical instrument
163 Lateral counter-surface of the surgical instrument
164 Distal through opening of the distal seat
165 Distal outer surface of the frame of the sterile adapter
166, 166' Spacer walls of the sterile adapter
167 Proximal portion of the transmission element of the backend
168 Distal portion of the linear actuator of the manipulator
169 Thickness of the membrane
170 Motor box or housing
171 Proximal end of the shaft
172 Distal end of the shaft
173 Outer margin of the membrane
174 Roll joint of the robotic surgery system 175 Arched edge
176 Anti-removal mechanism
z-z Proximal-distal direction
R-R Radial direction

The invention claimed is:

1. A sterile adapter for a robotic surgery system, suitable to transmit a plurality of linear actuation actions and a roll action from a non-sterile robotic manipulator system to a sterile surgical instrument having a backend portion and a shaft extending from said backend portion, the sterile adaptor comprising:

a frame for transmitting the roll action from the non-sterile robotic manipulator system to the sterile surgical instrument, the frame comprising:

a proximal coupling device, for coupling with the non-sterile robotic manipulator system; and a distal coupling device, for coupling with the sterile surgical instrument;

wherein said frame delimits a through opening between said proximal coupling device and said distal coupling device;

a membrane fixed to said frame, for transmitting through the thickness thereof the plurality of localized linear actuation actions from the non-sterile robotic manipulator to the sterile surgical instrument;

wherein:

said membrane is elastically stretchable with the purpose to result elastically biased towards a substantially flat configuration thereof, said stretchable membrane seals said through opening forming a distal cavity between said stretchable membrane and said distal coupling device;

said distal cavity includes substantially flat lateral guiding surfaces configured to mate with at least one lateral countersurface of said surgical instrument and is suitable for receiving at least a portion of the backend of the sterile surgical instrument;

said distal coupling device comprises at least one abutment surface facing said stretchable membrane and thereby at least partially delimiting said distal cavity; and said at least one abutment surface is suitable for a portion of the surgical instrument to abut thereon.

2. The sterile adapter according to claim 1, wherein said distal cavity includes a lateral opening designed for inserting said sterile surgical instrument into the sterile adapter.

3. The sterile adapter according to claim 1, wherein said distal cavity includes a second lateral opening suitable to access the distal cavity with the purpose of pushing said sterile surgical instrument out from said distal cavity of the sterile adapter.

4. The sterile adapter according to claim 1, wherein said membrane is in a single flat piece.

5. The sterile adapter according to claim 1, wherein said distal coupling device defines a distal seat having a distal through opening that opens distally outside of the distal cavity, and said distal through opening is substantially aligned with the through opening that is sealed by the stretchable membrane, and is coaxial with the through opening that is sealed by the stretchable membrane.

6. The sterile adapter according to claim 1, wherein said at least one abutment surface is beneath the stretchable membrane, and under the encumber of the membrane.

7. The sterile adapter according to claim 1, wherein said membrane has shape of a disc.

8. The sterile adapter according to claim 1, wherein said membrane is integrally mounted with said frame.

\* \* \* \* \*